United States Patent [19]

Clark et al.

[11] 4,221,567
[45] Sep. 9, 1980

[54] SAMPLING AND DETERMINATION OF DIFFUSIBLE CHEMICAL SUBSTANCES

[75] Inventors: Justin S. Clark; William D. Wallace; Frederick L. Farr, all of Salt Lake City, Utah

[73] Assignee: Intermountain Health Care, Salt Lake City, Utah

[21] Appl. No.: 863,802

[22] Filed: Dec. 23, 1977

[51] Int. Cl.² .................................................. G01N 33/16
[52] U.S. Cl. .................................... 23/230 B; 23/928; 128/635; 422/68
[58] Field of Search ............... 128/2 E, 2.1 E, 2 L, 128/2 G, 2.07, 635, 642; 204/195 B, 195 T; 23/232 R, 232 E, 230 B, 928; 73/16, 19, 23; 422/83, 98, 108, 110, 68

[56] References Cited

U.S. PATENT DOCUMENTS

| | | | |
|---|---|---|---|
| 3,438,241 | 4/1969 | McKinley, Jr. | 73/19 |
| 3,451,256 | 6/1969 | Kolodney | 73/19 |
| 3,512,517 | 5/1970 | Kadish et al. | 128/2 E |
| 3,639,829 | 2/1972 | Harnoncourt | 128/2 L X |
| 3,661,010 | 5/1972 | Neuwelt | 128/2 E X |
| 3,874,850 | 4/1975 | Sorenson et al. | 23/230 B |
| 3,983,864 | 10/1976 | Sielaff et al. | 128/2 L X |
| 4,016,863 | 4/1977 | Brantigan | 128/2 L X |
| 4,062,373 | 12/1977 | Clark et al. | 137/3 |
| 4,119,406 | 10/1978 | Clemens | 128/2 F X |

FOREIGN PATENT DOCUMENTS

306417 6/1971 U.S.S.R. ................................... 422/83

OTHER PUBLICATIONS

Veasy, G. et al., "A New System for Computerized Automated Blood Gas Analysis," Jrnl. of TCV Surgery, vol. 62, No. 6, Dec. 1971, pp. 914-918.

Walton, D. M. Continuous Monitoring of Blood pH, $pCO_2$, and $PO_2$ in Clinical Practice, Conf. 8th BSIS, Denv., Col. (4-6 May, 1970), pp. 155-158.

Primary Examiner—Robert W. Michell
Assistant Examiner—Francis J. Jaworski
Attorney, Agent, or Firm—Criddle & Western

[57] ABSTRACT

Method and system for sampling and determining chemical substances such as blood gases, in a fluid matrix, such as blood, by bringing the chemical substances into equilibrium with a liquid in a fiber probe, passing the equilibrated liquid to a sensor adjacent the equilibrium region and on into a hollow fiber line enclosed in a calibration chamber. Calibration of the sensors is accomplished by reversing the flow of liquid from the hollow fiber line to the sensors. In the system chemical substances for sensor calibration are provided by an electric proportioner whose output is continuously controlled by the output of the sensors such that the substances proportioned into a fluid in the calibration chamber surrounding the hollow fiber line are substantially the same as the substances within the matrix. The concentration of substances is determined by the output of the sensors and the amount of substances fed from the proportioner to the fluid surrounding the hollow fiber line. When the substances being measured are in equilibrium with both the matrix and fluid surrounding the hollow fiber line, a null response is obtained at the sensors.

14 Claims, 2 Drawing Figures

FIG. I

SAMPLING AND DETERMINATION OF DIFFUSIBLE CHEMICAL SUBSTANCES

BACKGROUND OF THE INVENTION

This invention relates to the sampling and determining of chemical substances by a self calibrating system. More particularly, this invention relates to a method of sampling and determining the concentration of diffusible chemical substances in a matrix wherein said determinations are made on a substantially continuous basis.

The determination of chemical substances such as blood gases by an in vivo monitoring system has been proposed by several different methods each of which has its inherent disadvantages.

An intermittent monitoring system for blood gases and pH is disclosed by Clark et al in U.S. Pat. Nos. 3,838,682 and 3,910,256. These patents disclose a system wherein blood is automatically and intermittently withdrawn from an arterial catheter and delivered to a fully automated blood gas analyzer. The system provides an reliable around the clock gas analysis system proven to be reliable for blood gas measurements. The main disadvantage of this system is the practical limitation on sampling frequency in that the system, especially in children, is limited by the blood loss and replacement problems as well as the amount of saline infusion required to maintain the patency of the catheter. A needed addition to the automated blood gas analysis concept is a practical continuous monitoring of the partial pressures of oxygen and carbon dioxide as well as other chemicals in the blood or other body fluids such as electrolytes and simple sugars. In addition, a system that does not require the withdrawal of blood would also be desirable.

Several in vivo methods of determining the partial pressures of blood gases have been taught in the prior art. Gardner et al, *The Journal of Thoracic and Cardiovascular Surgery*, Vol. 62, No. 6, pages 844–850 (1971) refer to a method of sampling blood gases in vivo using a Teflon-encased cannula. The coating material acts as a diffusion membrane and a mass spectrometer sampling apparatus containing a high-vacuum pump draws gas into the mass spectrometer from the tissues surrounding the cannula diffusing through the membrane coating in amounts which are purportedly proportional to the partial pressure in the tissue of the substance being monitored. The cost of a mass spectrometer and the size of the sample required are prohibitive for other than research use.

Brantigan U.S. Pat. No. 4,016,863 teaches an apparatus for the in vivo sampling of blood gases which allows the blood gases to diffuse through a gas permeable membrane and to come into equilibrium with a liquid contained within the membrane. The sampling is done on a "one shot" basis as the apparatus must be withdrawn from the subject and the equilibrated fluid analyzed elsewhere.

Myers et al, *Surgery*, Vol. 71, No. 1, pp 15–21, (1972), and Niinikoski et al, Surgery, Vol. 71, No. 1, pp 22–26, (1972), both teach methods of utilizing an implanted silicone polymer tube filled with saline as a diffusion fluid and allowing tissue gases to equilibrate through the tubing with the saline solution. The saline is left in the tubing sufficiently long to allow equilibrium to take place whereupon samples are withdrawn from the opposite end of the tubing for analysis. The requirements for making an incision and implanting the tubing along with the size and length of tubing implanted make these methods impractical.

Another in vivo method and apparatus for blood gas analysis is taught by Sielaff et al in U.S. Pat. No. 3,983,864 wherein a catheter containing a gas permeable membrane is inserted into an artery. A carrier gas such as helium is contained within the catheter and purportedly allows the blood gases to diffuse through the membrane and come into equilibrium with the carrier gas. By means of displacement the carrier gas containing the equilibrated gas is removed to another area for analysis. Distinct disadvantages are that the sampling is intermittent and the carrier gas also diffuses out of the membrane and into the blood.

OBJECTS AND BRIEF DESCRIPTION OF THE INVENTION

It is an object of the present invention to provide a method and system for the sampling and monitoring of diffusible chemical substances in a fluid matrix which is self calibrating.

It is also an object of the present invention to provide a method and system for the sampling and determination of diffusible chemical substances in a fluid matrix by tonometry utilizing a self calibrating microsensor system wherein the microsensor electrolyte is the same liquid as used for sampling, determination and calibration.

A further object of the present invention is to provide a method and system for substantially continuous sampling and determination of diffusible chemical substances in a body fluid by a self calibrating system.

A still further object of the present invention is to provide a method and system for continuously sampling and monitoring blood gases by a self calibrating system having an accuracy comparable or superior to standard laboratory instruments.

These and other objects may be accomplished by the method and system hereinafter described. A probe containing a liquid is inserted into the fluid matrix containing the diffusible chemical substances to be sampled and monitored. The probe consists of a permeable liquid filled membrane having a liquid inlet and a smaller impermeable tube for transporting the liquid outside of the equilibration field. A set of sensors are located adjacent to the equilibrium field interconnecting said field with a hollow fiber line enclosed in a calibration chamber.

In operation the probe containing the liquid, is placed in the fluid matrix and absorbs the chemical substances diffusing through the permeable membrane until equilibrium is reached in a relatively short period of time. The equilibrated liquid is transported to the sensors adjacent to the equilibration field. Preferably the sensors have been precalibrated. The response obtained at the sensors is indicative of the concentration of chemical substances in the liquid matrix and is stored in digital form. The equilibrated liquid is then passed to the hollow fiber line surrounded by the calibration chamber containing known concentrations of the chemical substances being monitored which have been fed to the calibration chamber by chemical feeding means in response to the stored electrical output of the sensors.

Calibration is achieved by reversing the flow of liquid from the hollow fiber line to the sensors where a readout is obtained and stored in digital form in a controller. Theoretically, the concentration of chemical substances in the calibration chamber is the same as in the fluid matrix.

It will be noted that the same liquid is used for both sampling and calibration procedures and as a common electrolyte for the sensors.

The calibration cycle consists of an initial two point calibration for each substance being monitored followed by frequent single point calibrations using equilibrated liquid from the hollow fiber line containing known equilibrated concentrations as close as possible to the actual values in the fluid matrix being measured. During the sampling procedure the sensors receiving fluid from the probe constantly and continuously measure and store the value of the chemical substances based on the most recently stored calibration data. During the same time, the chemicals fed to the calibration chamber surrounding the hollow fiber line are constantly followng the most recently measured concentrations from the matrix fluid which minimizes the subsequent calibration time. Obviously the more frequently calibrations are made the more accurate the system will be.

Distinct advantages emanating from the system are (a) steady state equilibrium for each measured chemical substance independent of the efficiency of the probe, (b) elimination of errors associated with the sensors being sensitive to more than one chemical substance and (c) elimination of errors due to non-linearities of the sensors.

The method and system described is especially useful for the in vivo monitoring of body fluids and especially blood. Diffusible substances which can be measured include ions, simple sugars such as glucose and especially blood gases such as $O_2$ and $CO_2$.

Prior art systems are generally capable of measuring gases only, however, the use of a liquid as the carrier presents several advantages. A carrier gas is incapable of carrying substances such as sugars and electrolytes. A carrier gas diffuses into the blood stream across the membrane. In a carrier gas system the gases diffusing through the membrane is not limited by the solubility of a liquid matrix, and therefore encounters a much higher equilibrium time. In the liquid system of the present invention the probe acts as an equilibrium device for gases, ions, simple sugars and the like, and the concentrations are a result of equilibration with a liquid of limited solubility such as a saline-bicarbonate liquid which reaches equilibrium much more rapidly than techniques requiring equilibrium of gases in the gas state. Moreover, the same liquid can be used for sampling, calibration, and as the sensor electrolyte.

When used for blood analysis no blood sample has to be drawn and no contamination of the blood by carrier gases or other foreign substances occurs. All parts of the system are miniaturized. The probe is inserted through a catheter into an artery. The microsensors are located adjacent the probe and preferably outside the body of a patient whose blood is being monitored and a microcalibration chamber containing the hollow fiber line lies adjacent to the microsensors. The monitoring procedure must be carried out under isothermal conditions or mathematical corrections must be made based on solubilities of monitored substances and temperature differences between the probe and tonometer.

The invention will become more apparent from the following detailed description with reference to the accompanying drawings.

DESCRIPTION OF THE INVENTION

Figure 1:
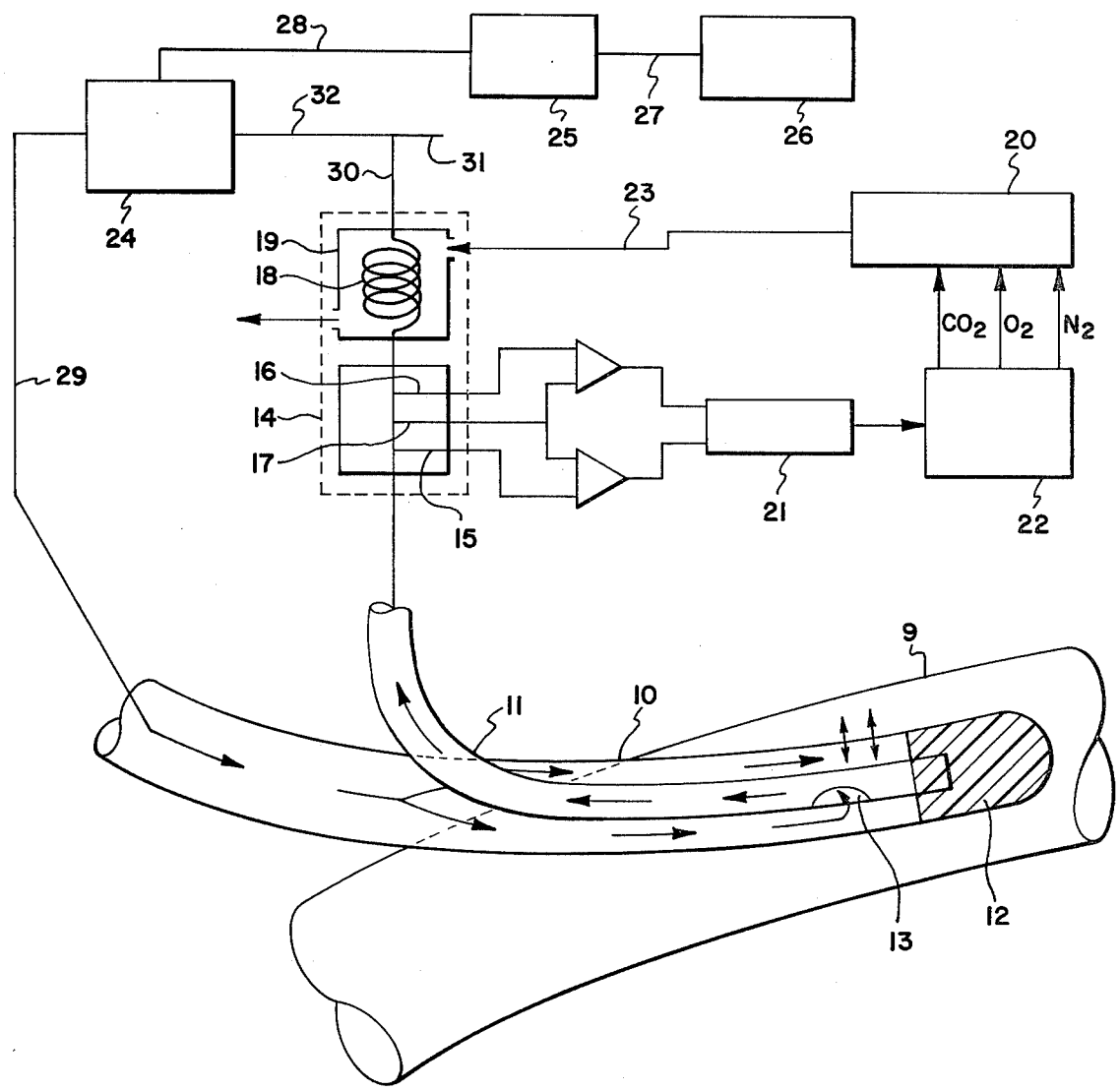
FIG. 1 illustrates an in vivo application of the invention wherein the probe is inserted into a blood vessel and illustrates the probe in an expanded portion as compared to the sensors, calibration chamber, and other external portions of the apparatus and sustaining equipment connected thereto.
Figure 2:
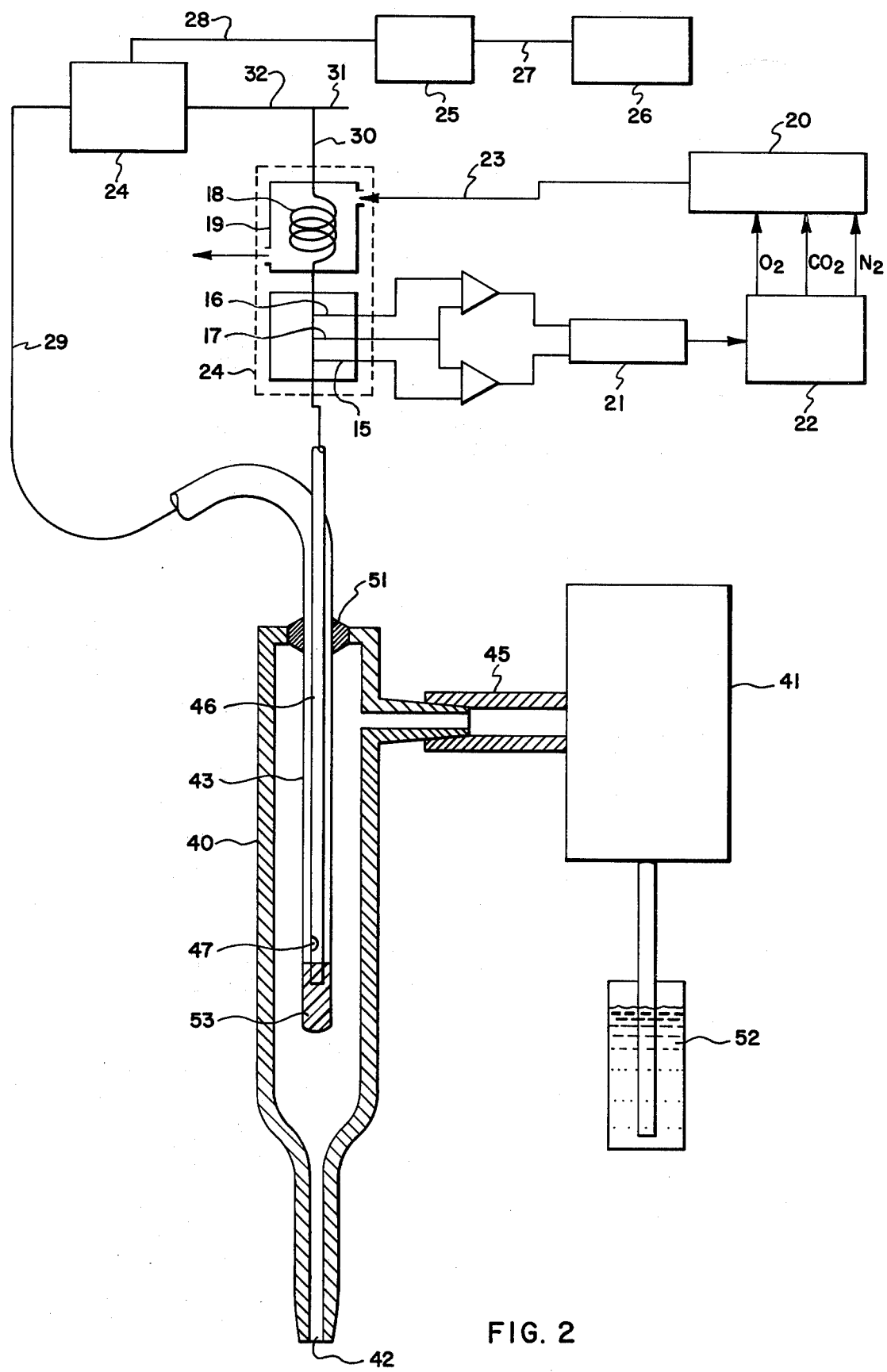
FIG. 2 illustrates an in vitro device for sampling and monitoring blood wherein the probe is greatly expanded in relation to the remainder of the illustrated equipment.

FIGS. 1 and 2 show two embodiments of the invention which are illustrative of the determination of the partial pressures of $O_2$ and $CO_2$ in the blood. However, the drawings and application could be readily modified for the determination of other chemical substances such as electrolytes, glucose, and other membrane permeable substances. Thus while the invention is described in terms of determining and calibrating the system in relation to blood gases, such description is not intended to be a limitation upon the scope of the invention.

There is shown in FIG. 1 a novel approach to the continuous blood gas monitoring which provides for the measurement of $PaO_2$ and $PaCO_2$ from a single probe with frequent calibration for both gases. At no time is the withdrawal of blood required. As illustrated, absolute accuracy for both gas measurements is equal to or superior to that obtained with standard laboratory equipment. Refering to FIG. 1, probe 10 constructed of a silicone polymer membrane or other inert fibrous material is preferably inserted through a percutaneous sheath covered catheter (not shown) into an artery.

The probe 10 is of small diameter having an outside diameter of from about 0.025 to 0.010 inches and an inside diameter of from about 0.012 to 0.008 inches and is permeable to $O_2$ and $CO_2$ but impermeable to liquids. Within probe 10 is a tube 11 constructed from materials such as stainless steel or glass. Tube 11 in impermeable or less permeable to the gases to be measured than probe 10. Tube 11 may, for example, be constructed from 33 to 36 gauge stainless steel having an outside diameter of from about 0.008 to 0.004 inches and an inside diameter of from about 0.004 to 0.002 inches. A liquid, such as a 9 percent normal saline-bicarbonate liquid solution, flows into the probe where $O_2$ and $CO_2$ equilibration takes place. Equilibrium time for $O_2$ varies from 1.5 to 1.75 seconds and for $CO_2$, from 0.5 to 1.5 seconds depending upon the thickness of the silicone polymer membrane. The gas impermeable tube 11 is sealed at the end of the probe in a silicone polymer rubber or other appropriate base 12 and is held permanently in position. An opening 13 is etched or cut away in the side of the gas impermeable tube 11 to allow the flow of equilibrated liquid from the gas impermeable tube 11 to the gas sensor chamber 14 located adjacent the probe and preferably outside the body. The sensors may be sized according to their location. Microsensors are preferably used since they are inexpensive and may be disposable. As illustrated the gas sensor or electrode chamber 14 contains an oxygen electrode 15, a carbon dioxide or pH electrode 16 and a reference electrode 17. The oxygen electrode must be flow-insensitive and may be a Clark type electrode of a 0.001 inch platinum wire molded into a glass tube and placed in a hypodermic needle for strength. The tip may be coated with collodion to reduce or eliminate flow artifact while retaining a sufficiently high frequency response. Small commercial glass electrodes may be used for sensing $CO_2$. Such electrodes may be replaced by a smaller size oxide of antimony or palladium. Chemically sensitive membranes may cover the electrodes or ion exchange electrodes may be used when sensing sugars, electrolytes, or other diffusible substances. The simplicity and low cost of the electrodes including a silver wire reference electrode, provide a practical option of a disposable probe including the sensors and electrode chamber 14. Although the means are not shown on the drawings, the probe may be disconnected at electrode chamber 14 and disposed of if desired. Also the electrode chamber 14 and electrodes 15, 16 and 17 may be detachable connected to the surrounding portions of the system and disposed of.

The fiber probe 10 is inserted through the catheter as described and, in the case of blood gas measurements, preferably extends past the end of the catheter situated in the artery. Since the gas impermeable tube 11 is made of a breakable material such as stainless steel or glass it is important that the end of the said tube be fused inside the probe 10 preferably in coiled form to increase elasticity and lessen the chance for breakage of tube 11.

The electrode chamber is connected to a hollow fiber line 18 located in an equilibrium or calibration chamber 19. The equilibrated liquid from probe 10 flows into electrode chamber 14 and comes in contact with electrodes 15, 16 and 17. Electrodes 15, 16 and 17 have preferably initially been calibrated by a two point calibration with fiber fluids containing $O_2$ and $CO_2$ at known relatively high and low partial pressures. Assuming a linear response, the output of each electrode when contacted by equilibrated fiber fluid is indicative of the partial pressures of the $O_2$ and $CO_2$ being monitored. Chemical feeding means 20 is controlled by controller 22 which contains feedback data directly related to the measured response at the electrodes supplies $O_2$ and $CO_2$ in known amounts to the calibration chamber 19. The equilibrated fiber fluid from the electrode chamber enters the hollow fiber line 18 and comes into equilibrium with the predetermined calibration gases in the calibration chamber which have been metered in to be present in the same partial pressures as contained in the blood measured by the electrodes.

Any suitable gas feeding means may be used. One that is particularly useful is claimed by Clark et al in Ser. No. 790,437 filed Apr. 25, 1977, now U.S. Pat. No. 4,062,373, as a Continuation-in-Part of Ser. No. 547,856 filed Feb. 7, 1975, and now abandoned, which applications are incorporated herein by reference. As illustrated the calibration gas is supplied to calibration chamber 19 via line 23 by an electrically controlled gas-proportioner 20 in response to feedback data stored in digital form in controller 22. The gas proportioner produces $O_2$ and $CO_2$ gas fractions precisely related to the electrical response relayed by sensors 15 and 16 which pass on electrical current to an A/D converter 21 which converts the signals from analog to digital form and in turn passes them on to controller 22 where they are stored. Controller 22, which may be a computerized device, in connection with proportioner 20 produces the desired mixture of $O_2$, $CO_2$ and $N_2$. Since the accuracy of the total system is determined by the accuracy of the gas proportioner, it is imperative that high accuracy in supplying all three gases to the calibration chamber be obtained with a minimum of time. Duty times on the order of 2 seconds are required by the gas proportioner to provide an accuracy of $\pm 0.001\%$.

The directional flow of fiber fluid in the probe 10 or impermeable tube 11 may be controlled by a bidirectional pump 24. When the system is in a monitoring mode, saline-bicarbonate solution is directed from supply source 25, which may contain a regulated supply of $O_2$ and $CO_2$ from gas supply 26 via line 27, into pump 24 from line 28 at a predetermined rate and thence through line 29 into probe 10. Preferably the saline-bicarbonate fiber fluid will be in fiber probe 10 long enough to become equilibrated with blood gases. The fiber fluid is then passed through the electrode chamber 14, hollow fiber line 18 into line 30. If complete equilibration with blood gases has taken place as indicated by frequent calibrations, the equilibrated saline-bicarbonate fluid may be disposed of through line 31. However, in most cases it will be desirable to recycle the probe liquid in one of two ways. If the signal received at controller 22 from the sensors indicate calibration is not required, the probe solution may be recirculated through line 31, pump 24, line 29 and back into probe 10 again. Recirculation may be continued constantly monitoring the equilibrated $O_2$ and $CO_2$ at the sensors based on the previous calibration. Preferably and more accurately, solution in hollow fiber line 18 equilibrated with known amounts of $O_2$ and $CO_2$ is withdrawn to electrode chamber 14 by reversing flow direction at pump 24. The electrodes are calibrated against the tonometered fiber fluid having known $O_2$ and $CO_2$ partial pressures and a readout of the response at the electrodes thus calibrated is obtained and stored in digital form by controller 22. The liquid then passes from the electrode chamber 14 back to probe 10 where equilibration with blood gases again takes place. Pump 24 is caused to reverse direction and the equilibrated fiber liquid is again brought into electrode chamber 14. The response obtained at the electrodes is relayed to controller 22 and stored in digital form. Controller 22 then compares the differences in readings between the equilibrated fiber fluid containing known amounts of $O_2$ and $CO_2$ and the equilibrated blood gases from the probe and causes proportioner 20 to adjust the gas mixture in the fluid in calibration chamber 19 in response thereto. The fiber fluid equilibrated with blood gases is then transferred to hollow fiber line 18 where it is again equilibrated with known amounts of $O_2$ and $CO_2$. The cycle is then repeated as many times as necessary until the electrode response from the liquid containing known amounts of $O_2$ and $CO_2$ from hollow fiber line 18 is the same as the response from the liquid from the probe equilibrated with blood gases. This procedure is particularly useful where equilibrium is not obtained the first time the liquid passes through the probe. By cycling the liquid back and forth, frequent calibrations are made and the more slowly diffusing gases are eventually brought into equilibrium. As a gas slowly comes into equilibrium the output at the sensors change thereby causing the controller 22 to adjust the gas proportioner output until electrode output nulls are obtained with respect to tonometered liquid from hollow fiber line 18 and probe liquid providing the equilibration temperatures in both the probe and hollow fiber line are equal.

Changes in the partial pressures of $O_2$ and $CO_2$ are determined rapidly by the above mentioned procedures and the changes can be monitored with minimum interruption for calibration. Calibrations preferably are made at regular intervals when the electrode outputs indicate the patient is stable. During rapid changes in partial pressures, calibrations are withheld to allow the system to follow the changes. Accuracy then depends upon the size of the change, electrode linearity, and the stability of the sensors since the last two point calibration. Generally, however, high accuracy is quite independent of electrode quality or linearity and is provided by adjusting the gas proportioner output, calibrating and measuring both tonometered and equilibrated probe liquids until a null response is obtained with respect to both values. The $PaO_2$ and $PaCO_2$ values are thus determined directly by the input to the gas proportioner 20. Accuracy therefore depends upon the tonometered liquid achieving precisely the same chemical state at equilibrium in hollow fiber line 18 as in the fiber probe 10 where the liquid equilibrates with the blood gas. Because the electrodes must detect only gas tension differences in the same liquid, accuracy depends upon the accuracy of the gas proportioner and on the sensitivity of the electrodes or sensors. Non-linearity, drift and flow sensitivity have minimal effect upon accuracy.

As mentioned, for the testing of blood gases, the probe is preferably a silicone rubber polymer. Copolymers of polycarbonates with dimethyl siloxane may also be used. For monitoring substances other than blood gases such as electrolytes and simple sugars, a more porous membrane such as a cellulose acetate fiber may be used as the probe cover or membrane.

FIG. 2 shows a similar system for the in vitro determination of chemical substances. While the system may be used to determine any diffusible substance as in FIG. 1 it will be described in connection with the determination of blood gases. The system as shown is capable of testing various blood samples under a constant temperature. The system may be flushed between samples with a saline solution and the fiber probe may or may not be replaced. As shown in FIGS. 2 the system consists of a cuvette 40, a peristaltic pump 41 which is bidirectional and will slowly pass blood or other body fluids through an opening 42 into the cuvette chamber. This provides a small continuous flow of fresh blood past a fiber probe 43 where equilibration with fiber liquid inside the probe takes place thus duplicating in vivo conditions at minimal blood flow. The saline fiber liquid is supplied directly to the probe in the cuvette as in FIG. 1. A saline wash liquid, similar to the probe liquid is supplied directly to the cuvette by a connecting line 45 which flushes the cuvette for additional sampling. The in vitro system operates on the same principles as already described for the in vivo system of FIG. 1. The fiber liquid enters a gas impermeable tube 46 via opening 47. The equilibrated fiber liquid enters electrode chamber 14 and comes in contact with the $O_2$ and $CO_2$ electrodes before passing to a hollow fiber line 18 as previously described. Monitoring, recirculating, cycling and calibration are carried out in the same manner as described in FIG. 1.

In operation, a blood sample is pumped through inlet 42 by pump 41 to surround probe 43. The walls of cuvette 40 are maintained at a constant temperature and the rate of blood flow through cuvette 40 is regulated by pump 41. Probe 43 is inserted into an opening in the top of cuvette 40. The opening is sealed with a silicone or rubber sealant 51 in fluid tight relationship. When the blood sample has been tested in the manner hereinbefore indicated the bidirectional pump is reversed drawing saline solution from reservoir 52 back through cuvette 40 thus washing the cuvette in preparation for another blood sample. The inner tube 46 is sealed in the end of probe 43 by a silicone or rubber plug 53.

In blood gas work the system offers versatility to encompass placement in any artery including the umbilical artery in neonates as well as percutaneous radial artery puncture in the full spectrum of pediatric patients or adults. The level of risk is no greater than that presented in conventional catheterization. However, the accuracy equals or exceeds that of standard laboratory blood gas instruments. A distinct advantage is the self calibration with a common liquid which is utilized in micro quantities.

The fiber probe can be inserted into an already positioned catheter to monitor any body fluid, the only limitations being on the sensitivity of the electrode sensors and the permeability of the probe to the chemical being measured. The fiber probe can be inserted into an already positioned umbilical arterial catheter or through a percutaneous radial catheter without limiting the ability to obtain blood samples through the catheter if desired. If the catheter placement site is in the radial artery, the fiber probe will advantageously be extended into the brachial artery to ensure that the blood surrounding the fiber has gas tensions representative of the source.

Fiber probes of silicone polymers and copolymers of polycarbonates and dimethyl siloxane have already been mentioned. Data using these materials obtained from human subjects involving two to six hours of perfusion show no thrombus formation inside the blood vessel near the fiber probes. Silicone polymers are known to have less thrombogenicity and tissue toxicity than most polymers used to interface with blood. If desired, heparinization of the fibrous material may also be done to produce even less thrombogenicity.

Although the present invention has been described with reference to blood gas monitoring for purposes of illustration, it is not so limited but may include the sampling and monitoring of any chemical substance diffusible through a membrane and capable of being monitored by a sensor.

We claim:

1. A method for determining the concentration of diffusible gaseous substances in a fluid matrix comprising:
    (a) introducing a probe into said fluid matrix, said probe containing an outer membrane permeable to the substances being determined and consisting of interconnected outer and inner chambers, the walls of said inner chamber being less permeable to the substances being determined than said membrane,
    (b) introducing an equilibration liquid of limited solubility to the substances being determined into said outer chamber in contact with said membrane,
    (c) allowing said gaseous substances to diffuse across said membrane and equilibrate with said equilibration liquid,
    (d) withdrawing said equilibration liquid equilibrated with said gaseous substances from said outer chamber through said inner chamber and introducing it to a sensor chamber containing sensors which are specific for the substances being determined, the electrical output of a specific sensor being representative of the concentration of a particular gaseous substance in said fluid matrix,
    (e) relaying the electrical output obtained at each sensor to controller means wherein it is stored.

(f) utilizing the stored signals in said controller means to actuate a chemical feeding means such that the chemical feeding means introduces a known concentration of gases being determined into a calibration chamber such that the concentration of each gas in the calibration chamber is known (g) passing said equilibration liquid from said sensor chamber to a hollow fiber means within the calibration chamber wherein the equilibration liquid equilibrates with the known concentrations of gaseous substances in said calibration chamber (h) passing the equilibration liquid from the hollow fiber means within the calibration chamber by reverse flow back to the sensor chamber whereby said sensors are calibrated with the equilibration liquid equilibrated with known concentrations of the gaseous substances being determined and the electrical output of each sensor calibrated is relayed to said controller means and stored.

2. A method according to claim 1 wherein the concentration of each gas in the calibration chamber is the same as that previously determined to be in the fluid matrix of the sensors and further comprising, (a) passing the equilibration liquid used to calibrate the sensors from the sensor chamber to the outer chamber of the probe and, (b) repeating steps (b) through (h) of claim 1 whereby the known concentrations of gaseous chemical substances in the equilibration means are altered in stages by the chemical feeding means until the stored sensor responses to equilibrated liquid from the inner chamber of the probe and from the hollow fiber means within the calibration chamber are the same.

3. A method according to claim 2 wherein the equilibration liquid serves as a common electrolyte for said sensors.

4. A method according to claim 3 wherein the body liquid is blood.

5. A method according to claim 4 wherein said equilibration liquid is a saline-bicarbonate solution.

6. A method according to claim 4 wherein the probe is inserted into an artery.

7. A method according to claim 6 wherein the gases being determined are oxygen and carbon dioxide.

8. A method according to claim 3 wherein the chemical feeding means is a gas proportioner.

9. A system for determining the concentration of diffusible gaseous substances in a fluid matrix comprising:

(a) a probe containing consentric outer membrane permeable to the substances being determined and consisting of an interconnected outer and inner chambers, the walls of said inner chamber being less permeable to the substances being determined than said membrane, the outer chamber containing liquid inlet means and the inner chamber containing liquid outlet means, (b) a sensing chamber in liquid communication with said inner and outer probe chambers containing sensors electrically sensitive to the gaseous substances in proportion to the concentrations thereof, (c) controller means adapted to receive, store and compare signals received from said sensors and issue commands responsive thereto, (d) hollow fiber means in liquid communication with the sensing chamber and surrounded by a calibration chamber, (e) chemical feeding means in electrical communication with said controller means adapted to feed variable known concentrations of the gaseous substances being determined into the calibration chamber as commanded by said controller means in response to the signals received from said sensors, and (f) bidirectional means interconnecting the liquid inlet to the probe to the hollow fiber means and adapted to regulate the direction and flow rate of liquid through the system.

10. A system according to claim 9 wherein the outer membrane of the probe is a silicone polymer or copolymer.

11. A system according to claim 10 wherein the chemical feeding means is a gas proportioner.

12. A system according to claim 11 wherein the sensors are electrodes specific to the determination of blood gases.

13. A system according to claim 12 wherein the blood gases are carbon dioxide and oxygen.

14. A system according to claim 13 wherein the probe is adapted to be inserted through a catheter and into an artery.

* * * * *